United States Patent
Brandeis

(10) Patent No.: US 9,770,246 B2
(45) Date of Patent: Sep. 26, 2017

(54) COUPLING DEVICES FOR INTERVENTIONAL DELIVERY SYSTEMS AND METHODS OF USING SUCH COUPLING DEVICES

(75) Inventor: Zeev Brandeis, Rosh HaAyin (IL)

(73) Assignee: V.V.T. Med Ltd., Kfar-Saba (IL)

( * ) Notice: Subject to any disclaimer, the term of this patent is extended or adjusted under 35 U.S.C. 154(b) by 389 days.

(21) Appl. No.: 13/021,817

(22) Filed: Feb. 7, 2011

(65) Prior Publication Data
US 2011/0196348 A1 Aug. 11, 2011

Related U.S. Application Data

(60) Provisional application No. 61/302,141, filed on Feb. 7, 2010, provisional application No. 61/302,143, filed on Feb. 7, 2010.

(51) Int. Cl.
*A61B 17/12* (2006.01)
*A61F 2/01* (2006.01)
*A61B 17/00* (2006.01)

(52) U.S. Cl.
CPC .. *A61B 17/12022* (2013.01); *A61B 17/12109* (2013.01); *A61B 17/12172* (2013.01); *A61F 2/01* (2013.01); *A61B 2017/00477* (2013.01); *A61B 2017/00623* (2013.01); *A61B 2017/00778* (2013.01); *A61B 2017/00867* (2013.01); *A61B 2017/12054* (2013.01); *A61F 2002/011* (2013.01); *A61F 2002/016* (2013.01); *A61F 2002/018* (2013.01); *A61F 2230/005* (2013.01); *A61F 2230/0006* (2013.01); *A61F 2230/008* (2013.01); *A61F 2230/0067* (2013.01)

(58) Field of Classification Search
CPC ................ A61F 2/01; A61F 2230/0067; A61F 2230/0093; A61F 2002/011; A61F 2/013
See application file for complete search history.

(56) References Cited

U.S. PATENT DOCUMENTS

| | | |
|---|---|---|
| 5,370,657 A | 12/1994 | Irie |
| 5,683,411 A | 11/1997 | Kavteladze et al. |
| 5,836,968 A | 11/1998 | Simon et al. |
| 6,267,783 B1 | 7/2001 | Letendre et al. |

(Continued)

FOREIGN PATENT DOCUMENTS

WO    WO 2006/017470    2/2006

OTHER PUBLICATIONS

Official Action Dated Dec. 12, 2012 From the US Patent and Trademark Office Re. U.S. Appl. No. 13/021,813.
Official Action Dated May 8, 2013 From the US Patent and Trademark Office Re. U.S. Appl. No. 13/021,813.
European Search Report and the European Search Opinion Dated May 25, 2011 From the European Patent Office Re. Application No. 1115365.4.

(Continued)

*Primary Examiner* — Katherine M Shi
*Assistant Examiner* — Michael Mendoza

(57) ABSTRACT

A coupling device, set to be linked to an interventional delivery system, for coupling and releasing a medical implant. The coupling device comprises a generally tubular channel sized and shaped to be conducted in an intravascular catheter and a pivot extended in and along the generally tubular channel having a distal end comprising a lower surface for applying pushing force a medical implant and an upper surface, mounted above the lower generally tubular surface and having at least one niche for receiving at least one anchoring element of the medical element so that a tip of each the anchoring element is placed between the lower and upper surfaces.

15 Claims, 8 Drawing Sheets

(56) References Cited

U.S. PATENT DOCUMENTS

| | | | |
|---|---|---|---|
| 6,551,340 B1* | 4/2003 | Konya et al. | 606/191 |
| 6,752,819 B1 | 6/2004 | Brady et al. | |
| 7,704,267 B2* | 4/2010 | Tessmer | 606/200 |
| 8,088,140 B2* | 1/2012 | Ferrera et al. | 606/200 |
| 2004/0082966 A1* | 4/2004 | WasDyke | A61F 2/01 |
| | | | 606/200 |
| 2004/0098030 A1 | 5/2004 | Makower et al. | |
| 2004/0153120 A1 | 8/2004 | Seifert et al. | |
| 2005/0038470 A1 | 2/2005 | Van der Burg et al. | |
| 2005/0222604 A1 | 10/2005 | Schaeffer | |
| 2008/0119867 A1 | 5/2008 | Delaney | |
| 2008/0294188 A1* | 11/2008 | Appling et al. | 606/200 |
| 2009/0131970 A1* | 5/2009 | Chanduszko et al. | 606/200 |
| 2010/0010532 A1 | 1/2010 | Vallabhaneni | |
| 2010/0324585 A1 | 12/2010 | Miles et al. | |

OTHER PUBLICATIONS

European Search Report and the European Search Opinion Dated May 26, 2011 From the European Patent Office Re. Application No. 1115365.4.
Communication Pursuant to Rules 70(2) and 70a(2) EPC and Reference to Rule 39(1) EPC Dated Aug. 16, 2011 From the European Patent Office Re. Application No. 11153553.0.
Communication Pursuant to Rules 70(2) and 70a(2) EPC and Reference to Rule 39(1) EPC Dated Aug. 16, 2011 From the European Patent Office Re. Application No. 11153565.4.
Notice of Allowance Dated Aug. 23, 2013 From the US Patent and Trademark Office Re. U.S. Appl. No. 13/021,813.
Communication Pursuant to Article 94(3) EPC Dated Jan. 19, 2016 From the European Patent Office Re. Application No. 11153565.4.

* cited by examiner

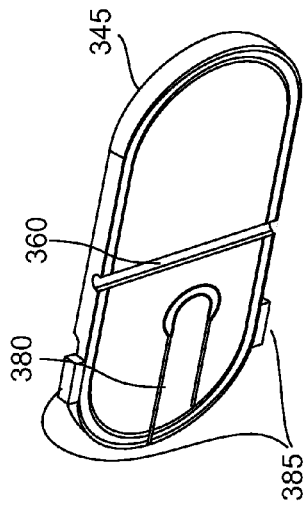
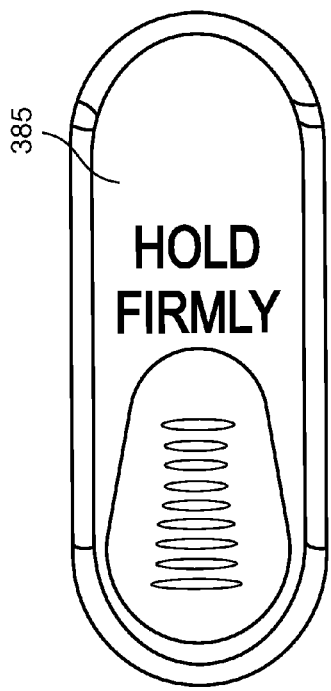
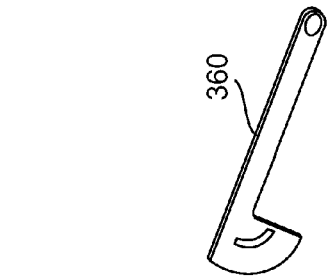
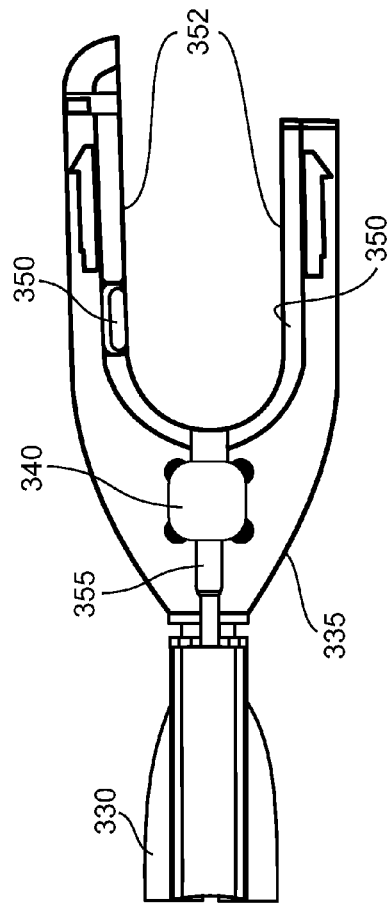

COUPLING DEVICES FOR INTERVENTIONAL DELIVERY SYSTEMS AND METHODS OF USING SUCH COUPLING DEVICES

RELATED APPLICATIONS

This application claims the benefit of priority under 35 USC 119(e) of U.S. Provisional Patent Application Nos. 61/302,141 and 61/302,143, both filed on Feb. 7, 2010. The contents of the above applications are incorporated herein by reference in their entirety.

FIELD AND BACKGROUND OF THE INVENTION

The present invention, in some embodiments thereof, relates to methods and devices for delivery of medical implants and, more particularly, but not exclusively, to methods and devices for delivery of medical implants into an intravascular lumen.

Various systems for delivery of vascular medical implants have been devised over the years in order to assist physicians in the implantation process within a patient, preferably in a minimally invasive manner. Most of the delivery systems include an elongated catheter that is used to access various passageways inside a patient's body.
Implants may include devices designed for compression into a small size tube or catheter to facilitate their introduction into the vasculature of the patient. The implants are subsequently expandable either to occlude defects or to contact the walls of the blood vessels.

A number of coupling devices have been developed to release the implant at the intravascular target area. An example for such a coupling device is described in U.S. Patent Application No. 2008/0154302, filed on Mar. 3, 2008, which describes a coupling device which is disposed at the distal end of an interventional delivery system for coupling to an implant. The coupling device has a first and second prong connected at one end. The other end of the prongs opens or closes to release or trap an object, e.g., a bead tethered from an implant. A slot at the distal end of the coupling device allows extra degrees of flexibility for the coupling device.

SUMMARY OF THE INVENTION

According to some embodiments of the present invention, there is provided a coupling device set to be linked to an interventional delivery system, for coupling and releasing a medical implant. The coupling device comprises a generally tubular channel sized and shaped to be conducted in an intravascular catheter and a pivot extended in and along the generally tubular channel having a distal end comprising a lower surface for applying pushing force on a medical implant and an upper surface, mounted above the lower generally tubular surface and having at least one niche for receiving at least one anchoring element of the medical element so that a tip of each the anchoring element is placed between the lower and upper surfaces.

Optionally, the generally tubular channel is sized and shaped to cover the pivot and the medical implant so as to fasten the at least one anchoring element between the upper and lower generally tubular surfaces.

Optionally, the pivot is coated with a polymer to provide a supportive structure.

Optionally, the medical implant is coupled to the pivot without and direct mechanical connection.

Optionally, the pivot is mechanically connected to a control mechanism facilitating the retrieving or repositioning of the medical implant into the generally tubular channel.

Optionally, the pivot is mechanically connected to a safety mechanism for requiring a verification action of the user before a deployment of the medical implant.

Optionally, the distal end is curved so that the tip is directed substantially toward the upper surface when respective the anchoring element being placed between the lower and upper surfaces.

According to some embodiments of the present invention, there is provided a method for coupling a medical implant. The method comprises providing a coupling device comprising a generally tubular channel sized and shaped to be conducted in an intravascular catheter and a pivot extended in and along the generally tubular channel having a distal end comprising substantially parallel lower and upper surfaces having a gap therebetween, the upper surface having at least one niche, placing at least one anchoring element of a medical implant in proximity to the distal end so that at least a tip of the at least one anchoring element implant is placed between the lower and upper surfaces and so that the at least one anchoring element passing through the upper surface and encircling the medical implant using the generally tubular channel.

Optionally, the medical implant has an elastic blocking element having compressed and uncompressed states, the encircling comprising covering the elastic blocking element in the compressed state.

More optionally, the method further comprises uncovering the at least one anchoring element so as to allow outward tilting thereof.

More optionally, the medical implant is discoupled by: uncovering the at least one anchoring element, and rotating the pivot in relation to the generally tubular channel.

More optionally, the placing comprises: attaching an implant adaptor containing the medical implant in front of distal end of the generally tubular channel, performing the placing, and pulling the pivot into the generally tubular channel.

According to some embodiments of the present invention, there is provided a coupling device set to be linked to an interventional delivery system, for coupling and releasing a medical implant. The coupling device comprises a generally tubular channel sized and shaped to be conducted in an intravascular catheter and a pivot extended in and along the generally tubular channel having a distal end comprising a fastening element for coupling with a complementary fastening element of a medical implant.

Optionally, the pivot, the fastening element, and the complementary fastening element have a common diameter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 8A-8D are graphic illustrations of various aspects of pivot holding apparatus section of a delivery rod handle, in accordance with an exemplary embodiments of the invention.

DESCRIPTION OF EMBODIMENTS OF THE INVENTION

Figure 1:
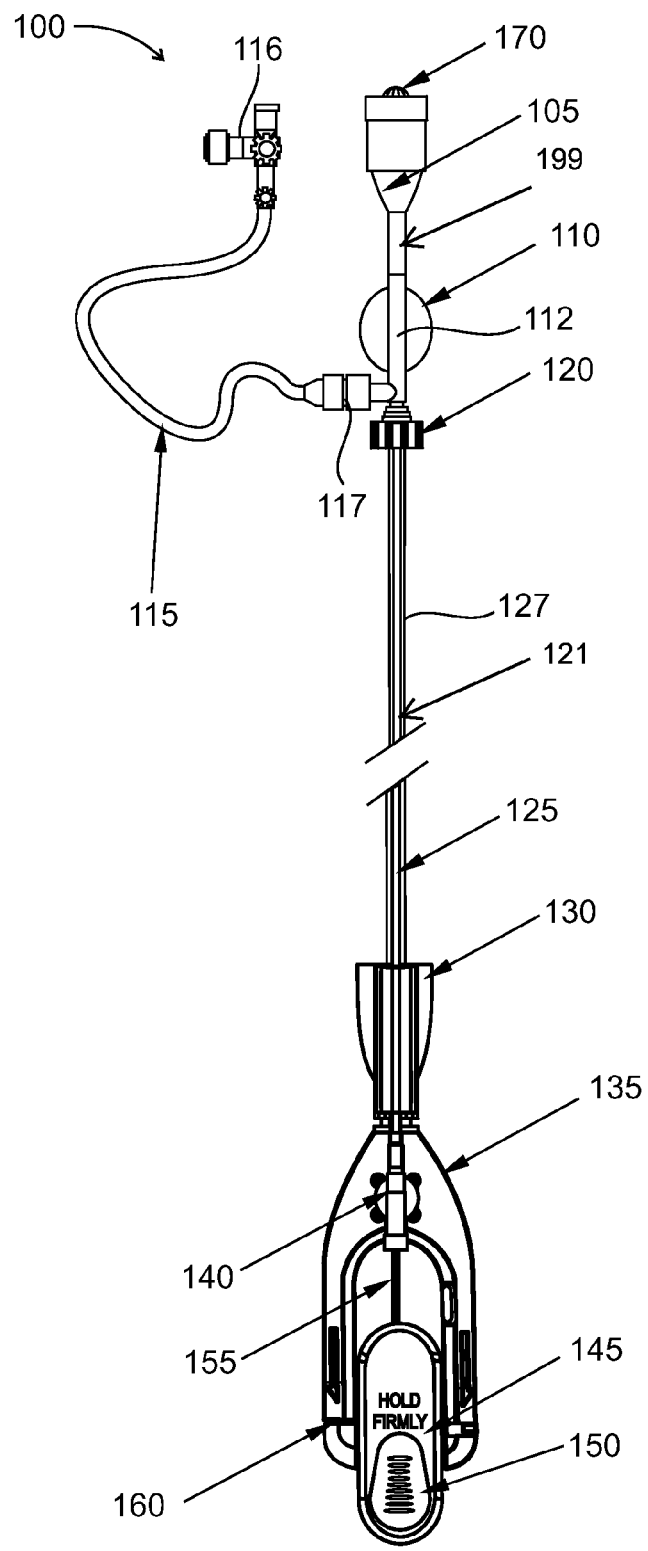
FIG. 1 is a coupling device disposed at the distal end of a catheter of an interventional delivery system, according to some embodiments of the present application.

The present invention, in some embodiments thereof, relates to methods and devices for delivery of medical implants and, more particularly, but not exclusively, to methods and devices for delivery of medical implants into an intravascular lumen.

According to some embodiments of the present invention, there are provided coupling devices, which are set to be linked to an interventional delivery system, for coupling and releasing medical implants, and methods of using thereof. For example, the coupling device includes a generally tubular channel sized and shaped to be conducted in an intravascular catheter and a pivot extended in and along the generally tubular channel. The pivot has a distal end with a lower surface for applying pushing force a medical implant and an upper surface having niche(s) for receiving anchoring element(s), such as elastic hooks, of a medical element, such as a blood vessel occluding implant. The surfaces are set so that a tip of each anchoring element may be placed in a gap therebetween and the generally tubular channel may be placed to encircle the gap. Another example is a coupling device having the generally tubular channel and a pivot having a distal end with a fastening element for coupling with a complementary fastening element of a medical implant. In this exemplary embodiment, the pivot, the fastening element, and the complementary fastening element have a common diameter.

Some embodiments of the present invention describe the control mechanism that allows releasing medical implants from such coupling devices.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates a location 199 of a coupling device, in accordance with some embodiments of the present application. The coupling device is disposed in a catheter 110 of an interventional delivery system 100 and provides a mechanism for coupling and releasing a medical implant 170 (partly shown) during an implantation process. The medical implant 170 has one or more anchoring elements, such as hooks, for anchoring it in an intravascular lumen. For example the medical implant 170 is a blood vessel occluding device, for example as defined in co-filed international patent application to Zeev Brandeis, titled intravascular devices for treating blood vessels and a method of using such devices, which the content thereof is incorporated herein by reference.

The coupling device includes a delivery rod 125 having a pivot 155 and a substantially tubular channel 121 which is set to be threaded in a catheter 110 of the interventional delivery system 100. The pivot 155 is extended along the generally tubular channel 110 and set to apply pushing force on the medical implant 170 that is coupled at its distal end, for example as described below. The pivot 155 is optionally covered by a strengthening polymer, such as nylon. The coupling device is set to lock the anchoring elements in an openable space which is formed between the pivot 155 and the substantially tubular channel 121.

As further described below, the proximal end of the pivot 155 is functionally coupled to a delivery control apparatus so as to allow using the pivot 155 for guiding and deploying the medical implant 170 that is connected thereto to a intravascular target area in a target blood vessel, such as a vein, during a treatment, such as a varicose vein treatment, sclerotherapy and/or the like.

Figures 2A, 2B:
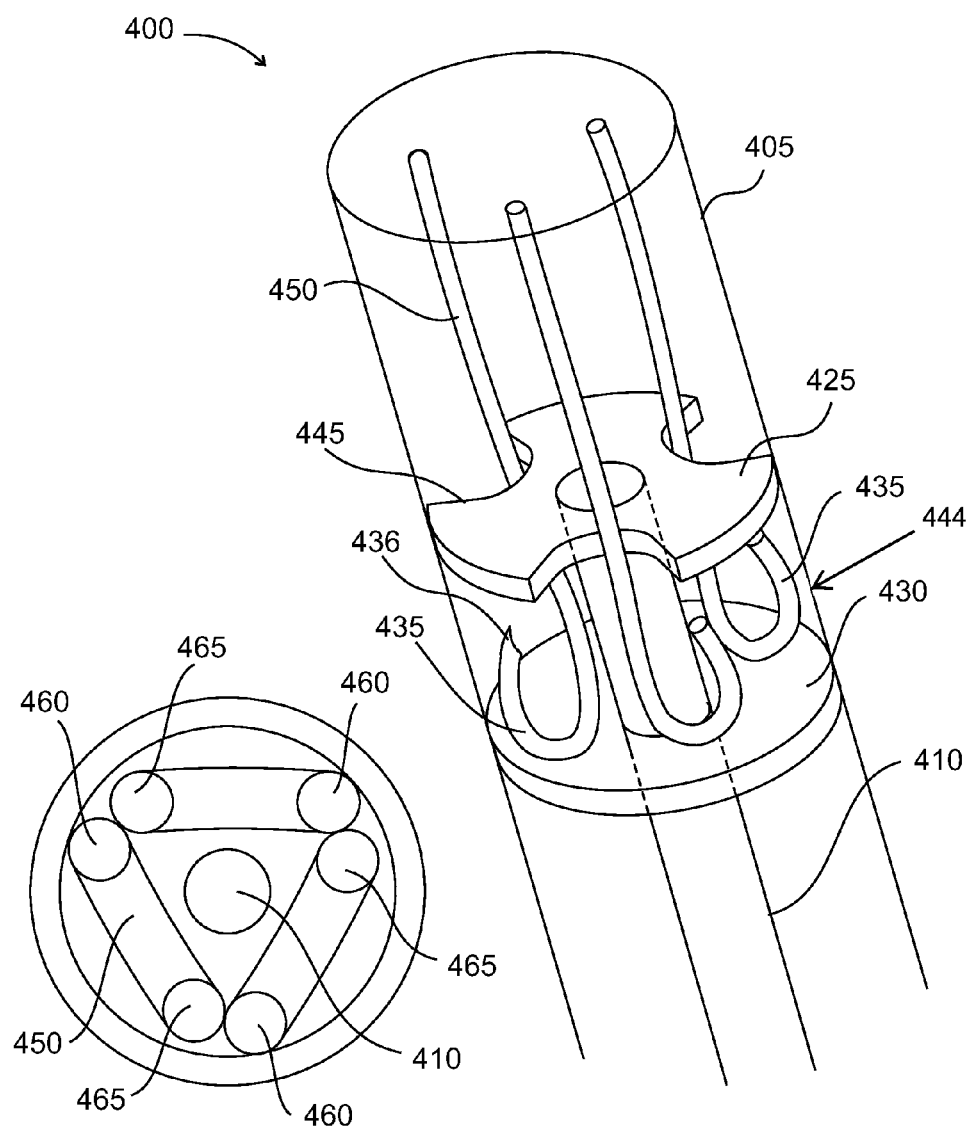
FIGS. 2A and 2B are lateral and top schematic illustrations of a coupling device, according to some embodiments of the present invention.

Reference is now also made to FIGS. 2A and 2B, which are lateral and top schematic illustrations of the distal end of a coupling device 400, according to some embodiments of the present invention. As shown at FIGS. 2A and 2B, the medical implant 170 has a plurality of anchoring elements 450. The anchoring elements 450 optionally have tilted and substantially vertical states. In the tilted state, the anchoring elements 450 are inclined away from the pivot 410 and in the substantially vertical state the anchoring elements 450 are substantially parallel to the pivot 410 (numeral 155 in FIG. 1). While the vertical state allows placing the medical implant 170 in the generally tubular channel 405 (numeral 121 in FIG. 1), the tilted state allows anchoring the medical implant 170 to the walls of the target blood vessel, for example as defined in co filed international patent application to Zeev Brandeis, titled intravascular devices for treating blood vessels and a method of using such devices, which the content thereof is incorporated herein by reference. Optionally, the anchoring elements 450 are constructed from shape memory materials, such as nickel titanium (Nitinol), to enable automatic switch between the states in an intravascular target area according to a controlled degree. At the distal end of the pivot 410, the coupling device 400 includes upper and lower plates 425, 430 having a gap 444 therebetween. For example, the pivot 410 may be permanently or detachably connected or coupled to the upper and lower plates 425, 430 and/or to a support element that is connected to the upper and lower plates 425, 430. The advancing and/or retrieving of the pivot 410 advances and/or retrieves the upper and lower plates 425, 430 and therefore advances, repositions and/or retrieves any element that is held in the gap 444. The gap 444 is sized to allow locating the distal ends of the anchoring elements 450, in a vertical state between the upper and lower plates 425, 430 so that, in use, for example during the release of the medical implant, the lower plate 430 applies pushing force on the anchoring elements 450 while the upper plate 425 covers the tips 436 of the anchoring elements 450. For example, FIG. 2B provides a cross sectional view of the tubular channel 405, where the distal end 435 of the anchoring elements 465 are depicted. As can be seen, the anchoring elements 450 pass via the upper plate 425 at points 460 and may be temporarily connected in a resting position, to prevent penetration of anchor tips 436 to surrounding vessels and/or blood vessel walls.

The medical implant 170 is coupled to the coupling device 99 when the anchoring elements 450 are locked between the upper and lower plates 425, 430 and the encircled by the tubular channel 405. It should be noted that in this embodiment, as the anchoring elements 450 are locked between the upper and lower plates 425, 430, the medical implant 170 is coupled to the pivot 410 without any direct mechanical connection. For example, when a practitioner loads the medical implant onto the interventional delivery system 100, she withdraws the generally tubular channel 405 to expose the gap 444 and places the distal end 435 of the anchoring elements 450 in the gap 444. Optionally, the upper plate 425 includes grooves 445 which allow threading the anchoring elements 450 therethrough, for example as shown at FIG. 2A. The upper and lower plates 430, together with the wall of the generally tubular channel 405, holds the anchoring elements 450 locked in the gap 444. In such a manner, the anchoring elements 450 may be released when the generally tubular channel 405 is retrieved from being placed in line with the gap 444, for example by retrieving the generally tubular channel 405 while maintaining the pivot 410 in place or pushing the pivot 410 while maintaining the generally tubular channel 405 in place. During the implantation, the withdrawing of the tubular channel 405 may be done by pulling the generally tubular channel 405 while holding the pivot 410 in position, by manipulating the pivot grip 345, the safety pin 160, and/or the delivery rod handle 135, for example as described.

Figures 3A, 3B:
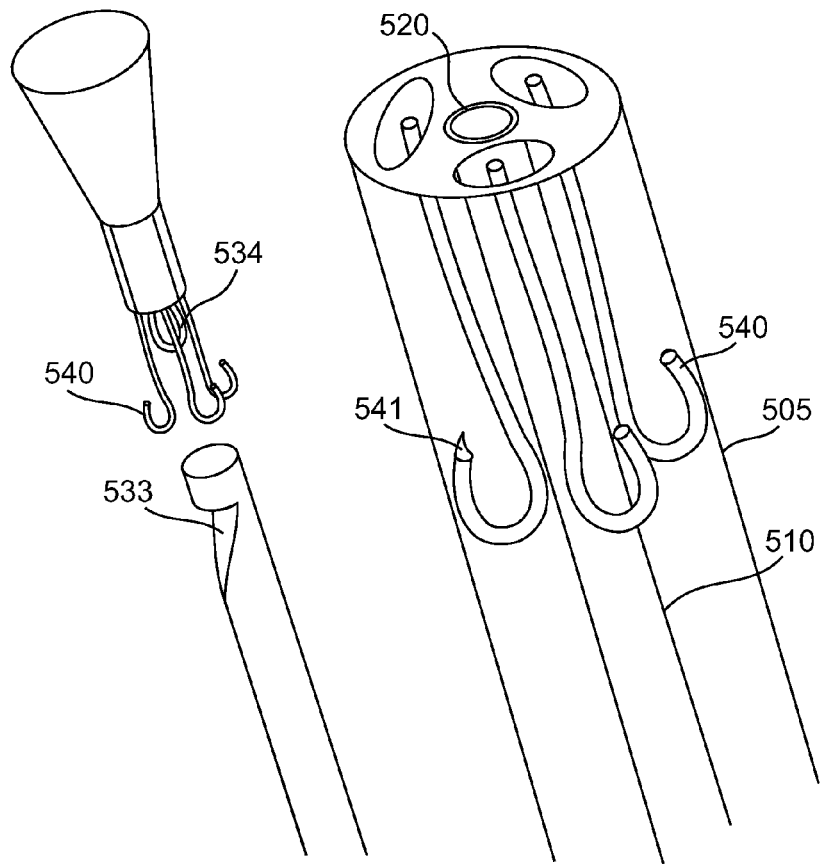
FIGS. 3A-3D are schematic illustrations of various components and angles of another exemplary coupling device, according to some embodiments of the present invention.

Reference is now also made to FIGS. 3A-3D, which are schematic illustrations of various components and angles of another exemplary coupling device 599, according to some embodiments of the present invention. Reference is also made to FIGS. 4A-4D, which are schematic illustrations of various components and angles of a similar coupling device 699, according to some embodiments of the present invention. As depicted in FIG. 3A/4A, and similar to the described above, the coupling device 599/699 is connected to the distal end of the pivot 510/610. As further described below, the proximal end of the pivot 510/610 is functionally coupled to a delivery control apparatus, for example as depicted in FIGS. 9A-9D. As depicted in FIG. 3B/4B, the distal end of the pivot 510/610 is coupled or comprises a first fastening element 533/633, such as a hook, for fastening, for example hooking onto a second fastening element/634, such as complementary hook, which is in proximity to anchoring element 540/640 of the medical implant 170. As depicted in FIG. 3B, the fastening elements 533 534 may be a groove, optionally triangular and a loop or vice versa, and/or, as shown at FIG. 4B, the fastening elements 633 634 may be two grooves, optionally rectangular which are complementary to one another. Fastening elements 533/633 and 534/634 are designed to be connected before initiating a treatment session, until the practitioner manipulates a pivot grip, safety pin, and/or a delivery rod handle, as described below with reference to FIGS. 9A-9D. The connection between the fastening elements 533/633 and 534/634 allows retrieving, repositioning and/or pushing the medical element 170. The fastening elements 533/633 and 534/634 are disconnected from one another after the anchoring elements 540/640 of the medical implant 170 are released into a deployment position. In some embodiments, the diameter of the fastening elements 533/633, 534/634, when they hold on another, is similar to the diameter of the pivot 510. Optionally, one or more of the fastening elements 533/633 534/634 are optionally made of metal, such as Nitinol for strengthening the connection therebetween. Of course, other shapes or types of hooking, attaching or locking mechanisms may be used.

Figures 3C, 3D:
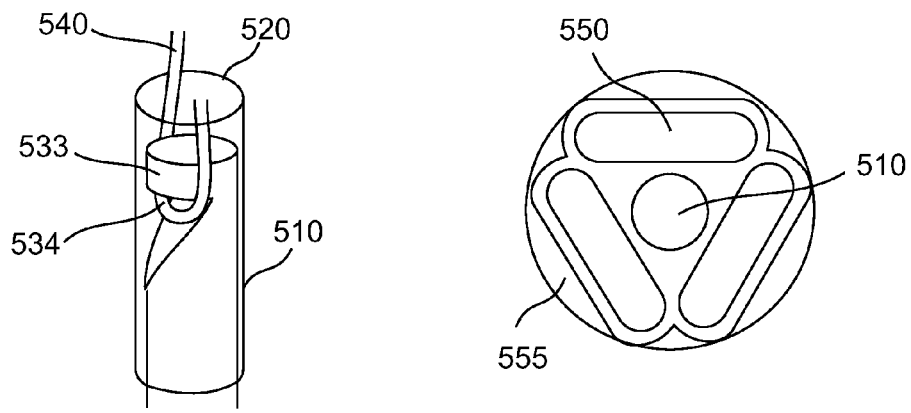
Figure 4B:
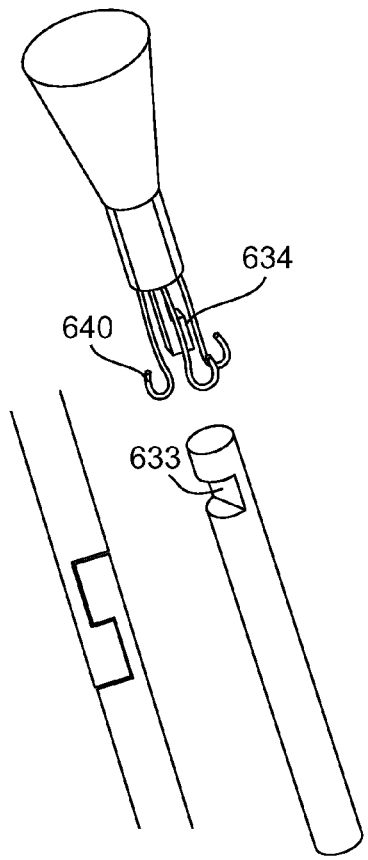
FIGS. 4A-4D which are schematic illustrations of various components and angles of a similar coupling device, with different fastening elements, according to some embodiments of the present invention.
Figure 4A:
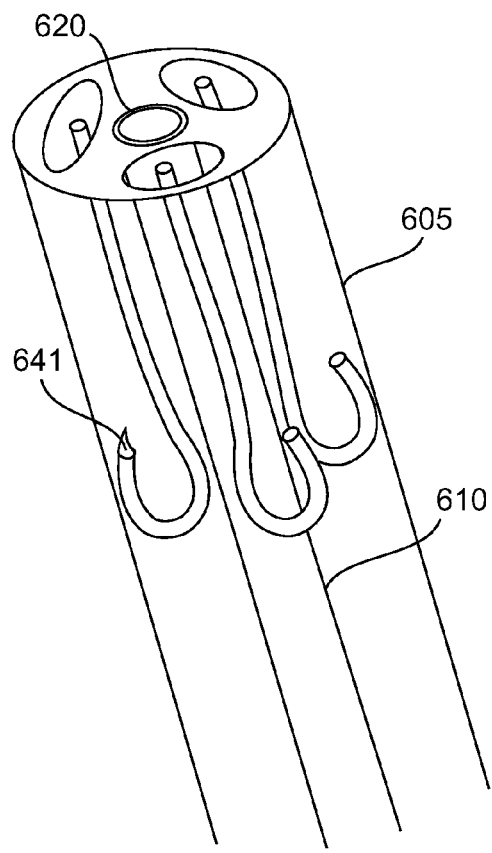
Figure 4D:
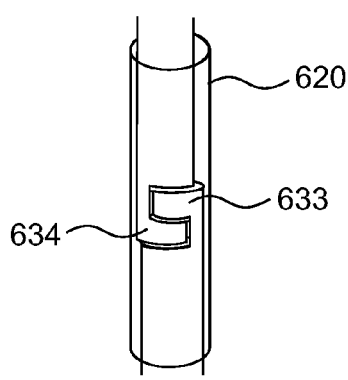
Figure 4C:
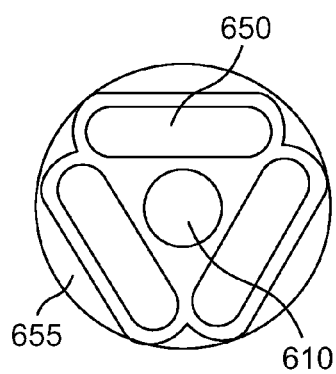

FIGS. 3C/4C provides a magnified horizontal cross sectional view, or profile, of the generally tubular channel 505/605, where the pivot 510 and the anchoring elements are depicted. Each figure depicts an exemplary pivot groove 555/655 and anchoring elements recesses 550/650.

FIG. 3D/4D provides a graphical perspective of the lumen of the generally tubular channel 505/605 at the area of the coupling devices, which enables strengthening the connection between fastening elements 533/633 and 534/634. The width of this segment may be between 5 millimeter (mm) and 15 mm.

Figure 5:
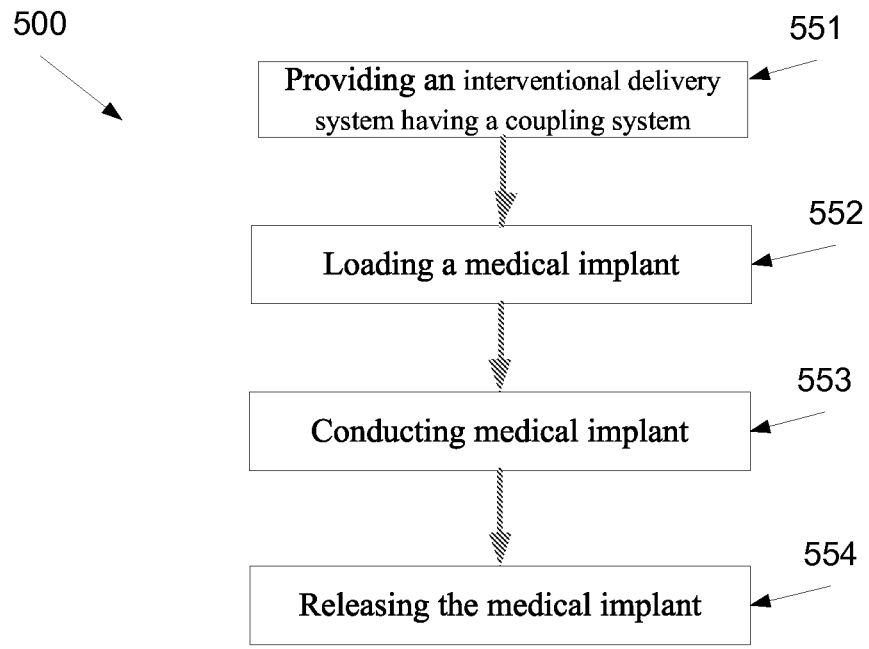
FIG. 5 is a flowchart of a method of placing a medical implant in a lumen of a blood vessel using an interventional delivery system, such as depicted in FIG. 1, according to some embodiments of the present invention.

Reference is now made, once again, to FIG. 1 and to FIG. 5, which is a flowchart of a method 500 of placing a medical implant in a lumen of a blood vessel using an interventional delivery system, such as depicted in FIG. 1, according to some embodiments of the present invention. The method is based, as shown at 551 on an interventional delivery system, such as 100, which includes a coupling device with delivery rod having a tubular channel and a pivot having a distal end, for example as depicted in FIGS. 2A and 2B.

As shown at 552, a medical implant, such as 170 is loaded onto the interventional delivery system 100, for example coupled to the coupling device thereof. During the loading, anchoring elements of the medical implant are optionally placed in a locking space of the coupling device where the distal ends of the anchoring elements are locked between upper and lower plates and the walls of the catheter 405 or as depicted in FIGS. 3A-3D and/or FIGS. 4A-4D where the distal ends of the anchoring elements are locked only by the walls of the catheter 405.

The loading is optionally done using an adaptor. In the interventional delivery system 100 depicted in FIG. 1 the distal end of the catheter 405 is connected to an adaptor 105 that is sized and shaped for holding the medical implant 170 prior to the loading thereof into the interventional delivery system 100. The adaptor 105 is optionally used as a container which encapsulates the medical implant 170 until opening of the package or kit which includes the delivery system 100. During the loading process, the adaptor 105 is placed at the distal end of the catheter 405. Then, the medical implant 170 is pulled into the catheter, optionally to an implant holding portion 112, such as a magazine, for example by a wire, such as the pivot 410. Once the medical implant 170 is in the implant holding portion 112, the adaptor is removed.

Figure 6:
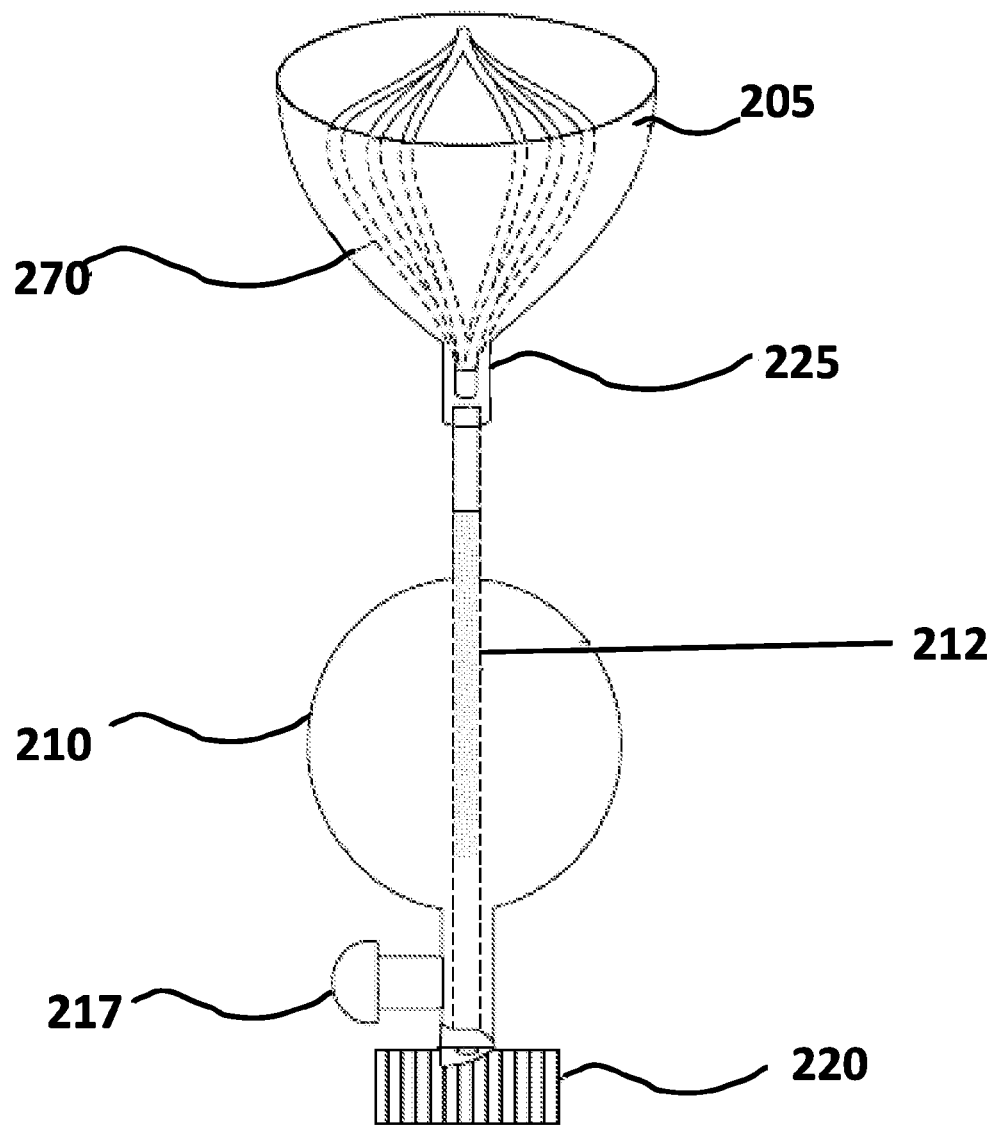
FIG. 6 is a schematic expanded view of a section of a catheter having an exemplary implant holding portion and an adaptor containing a medical implant, in accordance with an exemplary embodiment of the invention.

For example, reference is made to FIG. 6, which is a schematic illustration which depicts an expanded view of a section of a coupling device, in a catheter having an exemplary implant holding portion 200 and an adaptor 205, containing a medical implant 270, which is at a storage state and connected to the distal end of the catheter. As can be seen, the adaptor 205 is initially coupled to magazine holder 210 by a click connector 225. Once medical implant 270 is transferred into the holding section 212, where it may remain in a pre-deployment position, the adaptor 205 may be disconnected and discarded.

Figure 7:
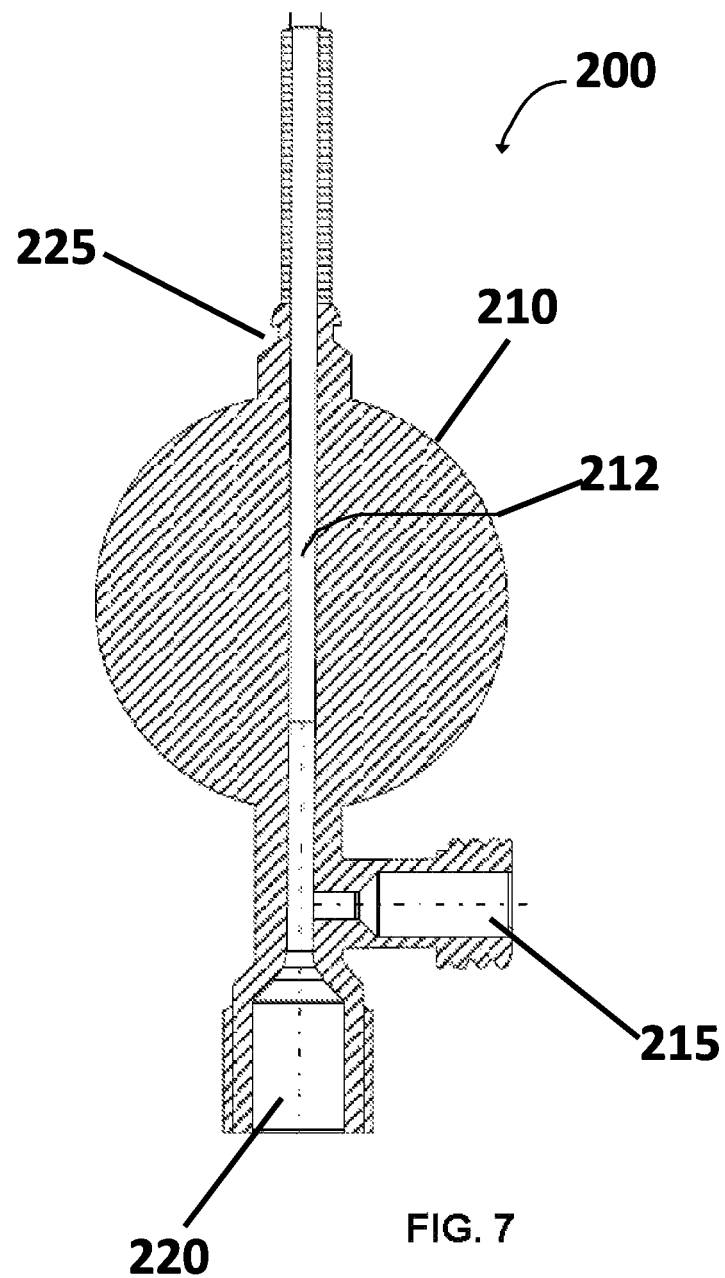
FIG. 7 is a graphic illustration of a section of the catheter which functions as a magazine, in accordance with an exemplary embodiment of the invention.

Reference is now made, once again, to FIG. 1. The holding section, referred to herein also as a magazine 112, is adapted to be loaded with the medical implant 170. For example, reference is also made to FIG. 7, which is a graphic illustration of a section of the catheter 200 which functions as a magazine, in accordance with an exemplary embodiment of the invention. As can be seen in FIG. 7, an implant holding portion or a grip 210 is designed for pulling or maneuvering the medical implant 170 from the adaptor 105 into a container area 212. The holding section 200 is typically coupled to a controllable haemostatic valve 220, a male Luer lock 215, and a click connector 225 to connect/disconnect the adaptor 105 and/or various introducing catheter elements or sheaths (not shown). Click connector 225 may be adapted to be used with different types of hubs and/or Luer Lock connectors. In some embodiments the click connector is connected with a holding cup and then with an introducing catheter or other catheter.

As shown at 553, after the medical implant 170 has loaded, for example into the magazine 112, it is conducted to an intravascular target area along one or more paths passing via one or more intrabody lumens, such as blood vessels. Then, it is released at the intravascular target area, as shown at 554. The conducting and the releasing are performed using the interventional delivery system 100.

Optionally, the conducting of the medical implant into the intravascular target area is supported by a practitioner that uses an Ultra sound tracking system to decide upon an entry point for the procedure. For example, a Micro Puncture set may be used to enter below the knee and/or above ankle using Ultra sound navigation. The micro puncture sheet may then be extracted, and a guiding wire may be inserted. For example, a 0.38 J guiding wire may be inserted into the Safenous vein, under Ultra sound guidance, until the desired location has been reached. The practitioner may then insert an introducing catheter and a dilator, such as cook flexor 6F, until the target area has been reached, typically distal to the desired location. The guide wire may then be retracted with the Dilator together.

Optionally, the interventional delivery system 100 includes a port 115, such as a side port, with three way stop cock 116 and Luer lock 117 for flushing, injecting or suctioning of liquids or other materials is connected to the magazine 112. This side port 115 may be used for connecting to one or more delivery syringes and/or catheters. A rotating screw, such as TBV Valve 120, is provided, to create a hermetic seal which enables connecting and/or disconnecting delivery catheter extension(s). A delivery rod 125 encased by delivery or introducer catheter portion 127 is provided. The delivery rod 125 includes the aforementioned pivot 155, which may be covered and/or coated, for example, by a polymer, to provide a supportive structure. As described above, the distal end of the pivot 155 is coupled to the medical implant 170 and the proximal end thereof is connected to a pivot holding apparatus. Optionally, the pivot holding apparatus includes a safety latch 130 to prevent releasing of the pivot 155 from the channel of delivery rod 125, and/or to stop unintended or premature releasing or deploying of the delivery rod from the delivery catheter. A delivery rod handle 135, delivery rod female Luer lock 140, and a pivot grip 145 with a pivot gripping mechanism 150 are provided, to enable controlled locking and releasing actions. A safety pin 160 may be used to prevent the release of grip 145 from rod handle 135, to prevent premature release of the medical implant 170 from the delivery rod, prior to final deployment. Delivery rod handle 135 is typically connected to distal back part of the delivery rod 125.

A practitioner releases the medical implant 170 by manipulating, for example rotating, the delivery rod handle 135. The man manipulation releases the coupling between the medical implant and the distal end of the pivot. For example, reference is now made to FIGS. 8A-8D, which are graphic illustrations of various aspects of pivot holding apparatus section of the delivery rod handle 135, in accordance with some embodiments of the present invention. As can be seen in FIG. 8A, the pivot holder includes A safety latch 330 which may be used to stop unintended or premature releasing of the medical implant 170 from the pivot of rod 355, a delivery rod handle 335, and a delivery rod female Luer Lock housing 340. The Luer Lock housing 340 may be adapted to be used with a variety of Luer Locks and Luer Lock connectors. FIG. 8B depicts a pivot grip 345 that enables controlled locking and releasing actions and pivot anchoring element 380, to fasten the end of the pivot, to prevent unintended deployment or release; and a safety pin 360 for securing final deployment of the medical implant 170. As can be seen in FIGS. 8B and 8C, safety pin 360 may be used to prevent the release of grip 345 from rod handle 335 and/or to prevent premature deployment of the medical implant prior to final deployment. A delivery rod handle 335 is typically connected to distal (back) part of the Delivery rod 125 (FIG. 1). The Delivery rod handle 335 may include rails 352 or indentations, and rail release points 350, to enable the controlled sliding or maneuvering of the pivot grip 345 into the Delivery rod handle. Pivot grip 345 may include leader elements 385 to enable smooth and controlled maneuvering along rails 352 towards rail release points 350.

As can be seen in FIG. 8D, gripping mechanism 385 may be coupled to pivot grip 345, to provide a clear, usable mechanism optionally with a safety warning and/or textual direction (e.g., "Hold Firmly") to help enable the practitioner to safely execute the Delivery rod controlling and anchoring processes.

It is expected that during the life of a patent maturing from this application many relevant devices and methods will be developed and the scope of the term a catheter, a rod, and a wire is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A coupling device, set to be linked to an interventional delivery system, for coupling and releasing a medical implant having a plurality of anchoring elements for anchoring the medical implant to the walls of a target blood vessel, comprising:
   a generally tubular channel sized and shaped to be conducted in an intravascular catheter; and
   a pivot extended in and along said generally tubular channel having a distal end comprising:
      a lower plate, and
      an upper plate, mounted above said lower plate and having a plurality of niches for receiving a plurality of anchoring elements of a medical element so that an anchor end of a hook formed at an anchor tip of each said anchoring element is:
         temporarily connected to a portion of said upper plate between two of said plurality of niches to prevent penetration of said anchor end to surrounding blood vessel walls, and
         placed between said lower and upper plates and covered by said upper plate;
   wherein said medical implant is coupled to said pivot without any direct mechanical connection so as to allow releasing of said plurality of anchoring elements for anchoring said medical implant the walls of a target blood vessel by retrieving said generally tubular channel while maintaining said pivot in place or pushing said pivot while maintaining said generally tubular channel in place;
   wherein each of a plurality of anchor tips of said plurality of anchoring elements are angled to fit into a triangle formed by a plurality of recesses around said pivot and below said upper plate.

2. The coupling device of claim 1, wherein said generally tubular channel is sized and shaped to cover said pivot and said medical implant so as to fasten said plurality of anchoring elements between said upper and lower plates.

3. The coupling device of claim 1, wherein said pivot is coated with a polymer to provide a supportive structure.

4. The coupling device of claim 1, wherein said pivot is mechanically connected to a control mechanism facilitating the retrieving or repositioning of said medical implant into said generally tubular channel.

5. The coupling device of claim 1, wherein said pivot is mechanically connected to a safety mechanism for requiring a verification action of the user before a deployment of said medical implant.

6. The coupling device of claim 1, wherein said distal end is curved so that said tip is directed substantially toward said upper plate when respective said anchoring element being placed between said lower and upper plates.

7. The coupling device of claim 1, wherein said pivot having a fastening element for coupling with a complementary fastening element of said medical implant.

8. The coupling device of claim 7, wherein said pivot, said fastening element, and said complementary fastening element have a common diameter.

9. The coupling device of claim 7, wherein said pivot, wherein said upper plate having a planar upper surface.

10. The coupling device of claim 1, wherein said lower plate is connected to said pivot so that when said pivot is pushed a pushing force is applied by said lower plate on distal ends of said plurality of anchoring elements.

11. A method for coupling a medical implant having a plurality of anchoring elements for anchoring the medical implant to the walls of a target blood vessel, the method comprising:

providing a coupling device comprising a generally tubular channel sized and shaped to be conducted in an intravascular catheter and a pivot extended in and along said generally tubular channel having a distal end comprising substantially parallel lower and upper plates having a gap therebetween, said upper plate having a plurality of niches;

placing a plurality of anchoring elements of a medical implant in proximity to said distal end so that at least an anchor end of a hook formed at a tip of each of said plurality of anchoring elements is:

temporarily connected to a portion of said upper plate between two of said plurality of niches to prevent penetration of said anchor end to surrounding blood vessel walls, and placed between said lower and upper plates and so that said plurality of anchoring elements passing through said upper plate; and encircling said medical implant using said generally tubular channel;

wherein said medical implant is coupled to said pivot without any direct mechanical connection so as to allow releasing said medical implant by retrieving said generally tubular channel while maintaining said pivot in place or pushing said pivot while maintaining said generally tubular channel in place;

wherein said lower plate is connected to said pivot;

wherein said anchor tip is adapted for anchoring said medical implant to the walls of a target blood vessel;

wherein each of a plurality of anchor tips of said plurality of anchoring elements are angled to fit into a triangle formed by a plurality of recesses around said pivot and below said upper plate.

12. The method of claim 11, wherein said medical implant having an elastic blocking element having compressed and uncompressed states, said encircling comprising covering said elastic blocking element in said compressed state.

13. The method of claim 12, further comprising uncovering said elements so as to allow outward tilting thereof.

14. The method of claim 12, wherein said medical implant is discoupled by:

uncovering said elements, and rotating said pivot in relation to said generally tubular channel.

15. The method of claim 12, wherein said placing comprises:

attaching an implant adaptor containing said medical implant in front of distal end of said generally tubular channel, performing said placing, and pulling said pivot into said generally tubular channel.

* * * * *